United States Patent [19]

Balzer

[11] Patent Number: 5,100,573

[45] Date of Patent: Mar. 31, 1992

[54] THICKENED SURFACTANT COMBINATION OF ALKYL OLIGOGLYCOSIDES AND CARBOXYMETHYLATED OXYETHYLATES

[75] Inventor: Dieter Balzer, Haltern, Fed. Rep. of Germany

[73] Assignee: Huels Aktiengesellschaft, Marl, Fed. Rep. of Germany

[21] Appl. No.: 440,214

[22] Filed: Nov. 22, 1989

[30] Foreign Application Priority Data

Feb. 25, 1989 [DE] Fed. Rep. of Germany ....... 3905939

[51] Int. Cl.$^5$ .................. C11D 3/22; C11D 1/74; C11D 17/00
[52] U.S. Cl. .................. 252/174.17; 252/108; 252/132; 252/134; 252/173; 252/174; 252/174.21; 252/174.22; 252/DIG. 5; 252/DIG. 13
[58] Field of Search .......... 252/174.17, 173, DIG. 5, 252/DIG. 13, 174.21, 174.22, DIG. 14, 108, 132, 134, 174

[56] References Cited

U.S. PATENT DOCUMENTS

| | | | |
|---|---|---|---|
| 4,089,945 | 5/1978 | Brinkman et al. | 424/164 |
| 4,242,215 | 12/1980 | Smid et al. | 252/100 |
| 4,483,787 | 11/1984 | Jones et al. | 252/551 |
| 4,536,318 | 8/1985 | Cook et al. | 252/174.17 |
| 4,668,422 | 5/1987 | Malik et al. | 252/174.17 |
| 4,732,696 | 3/1988 | Urfer | 252/174.17 |
| 4,770,804 | 9/1988 | Hentschel et al. | 252/75 |
| 4,992,263 | 2/1991 | Tesmann et al. | 424/63 |
| 5,034,159 | 7/1991 | Tesmann et al. | 252/551 |

FOREIGN PATENT DOCUMENTS

| | | |
|---|---|---|
| 0306843 | 3/1989 | European Pat. Off. |
| 1169496 | 11/1969 | United Kingdom |
| 1284791 | 8/1972 | United Kingdom |
| 8801639 | 3/1988 | World Int. Prop. O. |

*Primary Examiner*—Paul Liberman
*Assistant Examiner*—A. Beadles-Hay
*Attorney, Agent, or Firm*—Oblon, Spivak, McClelland, Maier & Neustadt

[57] ABSTRACT

Aqueous compositions containing alkyl oligoglycosides, unsaturated carboxymethylated oxyethylates, electrolyte and additives, which demonstrate a synergistic thickening effect. The aqueous compositions are useful as the basis of shampoos, bath and shower gels as well as other cosmetic formulations with increased viscosity.

10 Claims, No Drawings

THICKENED SURFACTANT COMBINATION OF ALKYL OLIGOGLYCOSIDES AND CARBOXYMETHYLATED OXYETHYLATES

BACKGROUND OF THE INVENTION

1. Field of the Invention

The invention concerns surfactant combinations as the basis for water-based shampoos, bath and shower gels as well as other cosmetic formulations, i.e. liquid cleaners or other systems for which an increased viscosity is necessary for application reasons.

2. Discussion of the Background

In the past, liquid cleaner systems were based predominantly on alkyl sulfates or alkyl ester sulfates, generally with a low degree of ethoxylation. In these cases, viscosity can be adjusted relatively easily by adding sodium chloride, ammonium chloride, optionally also combined with fatty acid diethanolamides and/or other additives. Although such formulations demonstrate satisfactory foaming and are inexpensive, they do, however, have the disadvantage of being very irritating to the skin as well as to the mucous membranes of the eyes, which is of significant importance in view of increasingly frequent, in some cases daily use. Because of the risk potential of trace contaminants of N-nitrosodiethanolamine, it is also desirable to have available formulations which are as free of nitrogen as possible (see Hamke Meijer, Seifen-Ole-Fette-Wachse 114, 159 (1988)).

Milder surfactant preparations which do not have the disadvantages listed above but can also be thickened easily are therefore desirable. Inexpensive surfactants which are gentle to the skin and mucous membranes cannot be sufficiently thickened with electrolytes (H. Meijer, Seifen-Ole-Fette-Wachse 113, 135 (1987) and H. Tesmann, Parfumerie und Kosemetik 68, 630 (1987)). Attempts have therefore been made to achieve sufficiently high viscosity or thickening by increasing the surfactant concentration or by means of limited partial substitution of the ether sulfate with a milder and toxicologically unproblematical surfactant (H. Meijer, loc. cit. and U.S. Pat. No. 3,038,862). This does not, however, deal with the disadvantages listed above in a satisfactory manner. Thickening by means of water-soluble polymers is not considered a suitable alternative, due to the influence on the foam quality.

Carboxymethylated oxyethylates are considered to be mild surfactants which are gentle to the skin and mucous membranes, and are described as very good in this regard (N.A.I., Seifen-Ole-Fette-Wachse 109, 353 (1983)). These oxyethylates have the decisive disadvantage that they cannot be thickened with usual electrolyte concentrations, or can only be thickened insufficiently (EP-A 0 176 151).

Alkyl oligoglycosides also demonstrate very good properties with regard to tolerance for the mucous membranes (A. D. Urfer et al., Poster presentation, Second World Conference on Detergents, Montreux, 1986). But the alkyl oligoglycosides, especially those with a degree of glycosidation of 1 to 1.45, prove to be completely unsatisfactory with regard to thickening with electrolytes. Such alkyl oligoglycosides are usually insoluble in water at concentrations below 10% by weight, or at least have low solubility, which results in very cloudy or even two-phase dispersions in the presence of electrolyte.

A need continues to exist, therefore, for surfactant combinations which can be thickened with electrolyte, which are gentle to the skin and mucous membranes, and which are extensively free of ether sulfates and surfactants containing nitrogen.

The use of combinations of alkyl polyglycosides or alkyl oligoglycosides with anionic surfactants has been known for a long time.

DRP 593,422, for example, describes the use of cetyl maltoside with common soap, U.S. Pat. No. 3,721,633 concerns the use of mixtures of alkyl polyglycosides with anionic synthetic surfactants, such as dodecyl benzenesulfonate, for example, and the Technical Bulletin Triton CG 100 of Rohm and Haas dated 1975 mentions a mixture of alkyl polyglycoside with lauryl ether sulfate, among other things.

WO 86/02943 describes the combination of alkyl monoglycosides and/or alkyl oligoglycosides with various anionic surfactants such as alkyl sulfates, alkyl ether sulfates, olefin sulfonates, paraffin sulfonates or alkyl benzene sulfonates, with the goal of increasing viscosity. Contrary to the present invention, the anionic surfactants claimed are not very gentle to the skin and mucous membranes, which is of significant importance.

The combination of alkyl polyglycosides with alkyl benzenesulfonate and with carboxymethylated alkanoloxyethylates, among other things, is mentioned in EP 0 070 075, where a clearly higher degree of glycosidation of the glycosides is present.

Thickening with electrolytes, which is demonstrated by the combinations of alkyl oligoglycosides and carboxymethylated alkenoloxyethylates according to the invention, is not present. The combinations of alkyl oligoglycosides with carboxymethylated alkyl phenoloxyethylates also cannot be thickened with electrolyte.

SUMMARY OF THE INVENTION

Accordingly, one object of the invention is a surfactant combination for bath gels, shampoos and cleaners comprising a) 3–30% by weight of a carboxymethylated alkenoloxyethylate or mixture of a carboxymethylated alkenol and alkanol oxyethylates,
b) 3–30% by weight of a alkyl oligoglycoside
c) 0.05–5% by weight electrolyte thickener, and
d) the remainder water and additives, as necessary, to make up to 100% by weight.

DETAILED DESCRIPTION OF THE PREFERRED EMBODIMENTS

It has now surprisingly found that the combinations of alkyl oligoglycosides and carboxymethylated alkenoloxyethylates, optionally combined with carboxymethylated alkanoloxyethylates, can be thickened extremely well by means of conventional electrolyte concentrations, in contrast to their individual components. There is a strong synergistic thickening effect. The solutions remain clear after the electrolyte is added, and demonstrate gel-like flow behavior, in some cases, even at concentrations of active detergent of only 10% by weight.

Carboxymethylated oxyethylates which may be used according to the invention correspond to the formula (I)

$$R-(OC_3H_6)_m(OC_2H_4)_nOCH_2COOM \qquad (I)$$

in which R stands for a linear or branched, saturated or unsaturated hydrocarbon group with 10 to 20 carbon atoms, an alkyl aromatic group with 7 to 18 carbon atoms in the straight-chain or branched, saturated or unsaturated alkyl group or mixtures of these, m stands for 0 to 10, n for 1 to 15, M stands for an alkali metal or alkaline earth metal, ammonium or alkyl ammonium ion. The oxyethylates based on saturated fatty alcohols are used only with oxyethylates based on unsaturated alcohols. Carboxymethylated oxyethylates based on hydrophobic fatty alcohols with 14 to 20 carbon atoms and m=0 are preferred. Carboxymethylated oxyethylates based on unsaturated fatty alcohols or mixtures of saturated and unsaturated fatty alcohols are especially preferred.

The carboxymethylated oxyethylates can, for example, be produced according to German Patent 2,418,444, by reaction of oxyethylates with the formula $R-(OC_2H_4)_nH$ or $R-(OC_3H_6)_m(OC_2H_4)_nH$ with a salt of chloroacetic acid, in the presence of an alkali metal hydroxide or other base. The reaction does not have to be quantitative, so that the carboxymethylated oxyethylate may be a mixture of initial oxyethylate and reaction product.

Depending on the use, the salt which is also formed, can in many cases remain in the product. Carboxymethylated oxyethylates based on oleyl alcohol, elaidyl alcohol, linoleyl alcohol, linolenyl alcohol, etc., as well as mixtures of these, also with long-chain alkanols, are particularly suitable for cosmetic formulations.

Oxyethylates with a degree of carboxymethylation of between 20 and 100% by weight are preferred. Particularly preferred is a degree of carboxymethylation of about 90% by weight.

Glycosides which may be used according to the invention are alkyl oligoglycosides, i.e., compounds with the formula (II)

$$R'-O-Z_n \qquad (II)$$

in which R' stands for a linear or branched, saturated or unsaturated aliphatic alkyl group with 8 to 16 carbon atoms or mixtures of these and $Z_n$ stands for an oligoglycoside group with an average n=1 to 1.45, preferably 1.1 to 1.45, hexose or pentose units or mixtures of these. Alkyl oligoglycosides with 9 to 14 carbon atoms are especially preferred.

The alkyl oligoglycosides used according to the invention can be produced entirely or in part on the basis of renewable raw materials, according to known methods. For example, dextrose is converted to butyl oligoglycosides mixtures with n-butanol, in the presence of an acid catalyst. These mixtures are reglycosylated to the desired alkyl oligoglycoside mixtures.

The formula of the products can be varied within certain limits. The alkyl group R' is determined by the selection of the long-chain alcohol. For economic reasons, surfactant alcohols which are accessible on an industrial scale, with 8 to 16 carbon atoms, e.g. oxoalcohols, Ziegler alcohols and alcohols from the hydrogenation of fatty acids or fatty acid derivatives are advantageous.

The alkyloligoglycosyl group $Z_n$ is determined by the selection of the alkyl hydrocarbon, on the one hand, and by the adjustment of the mean degree of oligomerization n, on the other hand, for example according to DE-OS 19 43 689. In principle, it is known that polysaccharides, oligosaccharides and monosaccharides, e.g. starch, maltodextrin, dextrose, galactose, mannose, xylose, etc. can be converted to alkyl oligoglycosides. Hydrocarbons, starch, maltodextrine and dextrose, which are available on an industrial scale, are especially preferred. Since the alkyl oligoglycosides which are economically interesting do not demonstrate regioselectivity and stereoselectivity, the alkyl oligoglycosides are always mixtures of oligomers, which in turn represent mixtures of various isomer forms. They are present alongside one another, with alpha and beta glycoside bonds, in pyranose and furanose form. The glycoside bonding between two saccharide groups may also be different.

Alkyl oligoglycosides used according to the invention can also be produced by mixing alkyl oligoglycosides with alkyl monoglycosides. The latter can be obtained or enriched from alkyl polyglycosides, e.g. according to EP-A 0 092 355, by means of polar solvents such as acetone.

The amount ratios for combinations of alkyl oligoglycoside and carboxymethylated oxyethylates according to the invention are between 5:1 and 1:10. Ratios between 2:1 and 1:5 are preferred. The concentrations in aqueous formulation are between 5 and 30% by weight active substance, preferably between 7 and 20% by weight.

Electrolytes are suitable as thickeners in the invention. These electrolyte thickeners are, for example, sodium chloride, ammonium chloride, sodium sulfate, magnesium sulfate, etc.

The combinations of alkyl oligoglycosides and carboxymethylated oxyethylates according to the invention are usually sufficiently foamy, as a function of their use. If greater foaming is desired, the addition of small amounts (maximum of 5% by weight) of strongly foaming additives is recommended. Strongly foaming anionic surfactants, such as organic sulfates or sulfonates, for example, as well as sorbitan esters, can be used.

The amount ratios of these auxiliary surfactants to the composition according to the invention are generally about 1:9 to about 2:8. In some cases, but these will be rare in view of their environmental impact, it can be useful to also add fatty acid amides in small amounts.

Further possible additives, as a function of the use, are small amounts of polymers such as polyethylene oxide, chelate formers, preservatives, fragrances, etc.

The effective thickening of the compositions of the invention is shown by the following examples. Thickening was demonstrated with viscosity measurements in a rotation viscosimeter (Haake RV 20) at 20° C. under defined shear rates. For formulations with high structural viscosity, the mean viscosities are reported at shear rates between 3 and 10 sec$^{-1}$, in other words, under conditions which approximately correspond to the movement which takes place when a fluid flows out of a plastic bottle with an average-size opening. The degree of carboxymethylation of the carboxymethylated oxyethylates is about 90%.

Other features of the invention will become apparent in the course of the following descriptions of exemplary embodiments which are given for illustration of the invention and are not intended to be limiting thereof.

EXAMPLES

Example 1 (according to the invention)

In a glass vessel, 5.5 g carboxymethylated Ocenol 80/85 oxyethylate Na salt* was stirred together with 4 mol ethylene oxide/mol salt, 9.26 g $C_{12}C_{13}$-alkyl liogoglycosides with a D.P. of 1.4 (determined via $^1$H-NMR) as well as 85.24 g distilled water. The carboxymethylated oxyethylate contained 0.5 g NaCl and the alkyl oligoglycoside contained 4.26 g water, so that the content of active detergent was 10% by weight. The mixture was heated, and resulted in a solution that was still clear after several days. The same was also true for higher contents of NaCl, up to 3% by weight. The viscosity as a function of the NaCl content is summarized in the following table:

|  | NaCl (% by weight) | | | | |
| --- | --- | --- | --- | --- | --- |
|  | 0.5 | 1 | 1.5 | 2.0 | 3.0 |
| η at 25° C. (mPa · s) | 2 | 10 | 115 | 580 | 2,800 |

*Ocenol 80/85: oleyl-cetyl alcohol mixture from the Henkel company

Example 2 (comparison example)

This example shows that a 10% solution of carboxymethylated Ocenol 80/85 oxyethylates with 4 mol ethylene oxide/mol (11.0 g per 100 ml) was not thickened by adding NaCl, or only thickened slightly (see Table below). This solution was also clear.

|  | NaCl (% by weight) | | | |
| --- | --- | --- | --- | --- |
|  | 0.5 | 1 | 1.5 | 2.0 |
| η at 25° C. (mPa · s) | 1 | 4 | 6 | 31 |

Example 3 (comparison example)

This example shows that a 10% solution of a $C_{12}C_{13}$-alkyl oligoglycoside with a degree of glycosidation (D.P.) of 1.4 (=18.52 g/100 ml) cannot be thickened with electrolyte.

|  | NaCl (% by weight) | | | |
| --- | --- | --- | --- | --- |
|  | 0 | 1 | 2 | 3 |
| η at 25° C. (mPa · s) | 10 | 2 | 5 | 6 |

Example 4 (according to the invention)

5.5 g carboxymethylated Ocenol 80/85 oxyethylate with 3 mol ethylene oxide/mol (contains 10% by weight NaCl) and 10.6 g $C_{10}C_{12}$-alkyl oligoglycoside with a degree of glycosidation of 1.3 (active content 47% by weight) were dissolved in 83.9 g water, while heating. Subsequently, NaCl was added.

The viscosity measurements of the clear solution with 10% by weight active detergent as a function of the NaCl content yielded the following results:

|  | NaCl (% by weight) | | | | |
| --- | --- | --- | --- | --- | --- |
|  | 0.5 | 1 | 1.5 | 2.0 | 2.5 |
| η at 25° C. (mPa · s) | 25 | 360 | 660 | 2,730 | 1,900 |

Example 5 (according to the invention)

5.5 g carboxymethylated Ocenol 80/85 oxyethylate with 4 mol ethylene oxide/mol and 10.4 g $C_{12}C_{14}$-alkyl oligoglycoside with a degree of glycosidation of 1.3 were dissolved in 84.1 g water, and then, NaCl was added, until the clear, somewhat gel-like solution contained 1.5% by weight NaCl. The concentration of active detergent was 10% by weight. The viscosity at shear rates between 3 and 10 sec$^{-1}$ was 3,500 mPa.s.

Example 6 (according to the invention)

5.6 g carboxymethylated Ocenol 110/130* oxyethylate with 5 mol ethylene oxide/mol and 10.4 g $C_{12}C_{14}$-alkyl oligoglycoside with a degree of glycosidation of 1.3 were dissolved in 84 g water and then mixed with NaCl. The content of active detergent was 10% by weight. The viscosity measurements, as a function of the NaCl concentration of the system, yielded the following results:

|  | NaCl (% by weight) | | | | |
| --- | --- | --- | --- | --- | --- |
|  | 0.5 | 1.0 | 2.0 | 3.0 | 4.0 |
| η at 25° C. (mPa · s) | 7 | 30 | 440 | 2,600 | 4,500 |

*Ocenol 110/130 is oleyl-linoleyl alcohol from the Henkel company

EXAMPLE 7 (according to the invention)

5.4 g carboxymethylated dodecylphenol oxyethylate with 6 mol ethylene oxide/mol and 10.4 g $C_{12}C_{14}$-alkyl oligoglycoside (D.P.=1.3) and 1.4 g NaCl were dissolved in 83 g water. The viscosity of solution, which contained approximately 10% by weight active detergent, was 1,400 mPa.s.

Example 8 (according to the invention)

4.2 g carboxymethylated Ocenol 80/85 oxyethylate with 5 mol ethylene oxide/mol, 1.4 g carboxymethylated $C_{16}C_{18}$ tallow fatty alcohol oxyethylate with 5 mol ethylene oxide/mol and 10.4 g $C_{12}C_{14}$ oligoglycoside (D.P.=1.3) were dissolved in 84 g water, and then NaCl was added. The subsequent viscosity measurements of the clear solution, which contained 10% by weight active detergent, was thickened by means of added electrolyte according to the invention.

Example 9 (according to the invention)

2.8 g carboxymethylated Ocenol 80/85 oxyethylate with 4 mol ethylene oxide/mol, 2.8 g carboxymethylated $C_{16}C_{18}$ tallow fatty alcohol oxyethylate with 4 mol ethylene oxide/mol and 10.4 g $C_{12}C_{14}$ oligoglycoside (D.P.=1.3) were dissolved in 84 g water, and then NaCl was added. The viscosity of the gel-like solution (10% by weight active detergent, 3% by weight NaCl) was 4,800 mPa.s.

Example 10 (according to the invention)

8.2 g carboxymethylated Ocenol 92/96 oxyethylate Na salt with 4 mol ethylene oxide/mol., 5.2 g $C_{12}C_{14}$ alkyl oligoglycoside (D.P.=1.25) were dissolved in 86.6 g water. Then NH$_4$Cl was added at a concentration of 2% by weight. Another 0.6% by weight NaCl are contained in the mixtures, coming from the carboxymethylated oxyethylate. The viscosity of the clear solution, which contains 10% by weight active detergent, was 11,000 mPa.s.
*Oleyl alcohol from the Henkel company Example 11 (according to the invention)

5.4 g carboxymethylated nonylphenol oxyethylate, which was first reacted with propylene oxide (3 mol/mol) and then with 6.1 mol ethylene oxide, 10.4 g $C_{12}C_{14}$ alkyl oligoglycoside (D.P.=1.3) and 2 g NaCl were dissolved in 86.5 g water. The clear solution contained 10% by weight active detergent and demonstrated a viscosity of 750 mPa.s.

Example 12 (according to the invention)

4.3 g carboxymethylated Ocenol 80/85 oxyethylate with 4 mol ethylene oxide/mol, 8.5 g $C_{12}C_{14}$ alkyl oligoglycoside (D.P.=1.3) and 2.8 g MARLINAT® 242 $C_{12-14}$ alkanol ether sulfate with 2 mol ethylene oxide/mol and 2 g NaCl were dissolved in 82.4 g water. The viscosity measurement of the solution showed 2.750 mPa.s, the foaming capacity—measured in a manual perforated plate foaming apparatus of 250 ml with 1 g/liter active detergent in water at 12° dh—resulted in 285 ml foam, measured 30 sec after foam production stopped. A shampoo available on the market (Rilanet ® treatment shampoo) resulted in 260 ml foam at the same concentration of active detergent.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A surfactant composition, comprising:
   a) 3-30% by weight of a carboxymethylated oxyethylate having the formula (I)

$$R-(OC_3H_6)_m(OC_2H_4)_nOCH_2COOM \qquad (I)$$

wherein R is a linear or branched, unsaturated aliphatic group with 10 to 20 carbon atoms, m is 0 to 10, n is 1 to 15, M is an alkali metal, alkaline earth metal, ammonium or alkyl ammonium ion, with the degree of carboxymethylation being between 20 and 100% by weight,
   b) 3-30% by weight of an alkyl oligoglycoside,
   c) 0.05-5% by weight of an electrolyte thickener, and
   d) the remainder water and conventional additives up to 100% by weight.

2. The surfactant composition of claim 1, wherein R is selected from the group consisting of a monounsaturated, polyunsaturated hydrocarbon group and mixtures thereof.

3. The surfactant composition of claim 1, wherein said carboxymethylated oxyethylate further comprises a mixture of compounds having the formula (I)

$$R-(OC_3H_6)_m(OC_2H_4)_nOCH_2COOM \qquad (I)$$

wherein R is both a linear or branched, saturated aliphatic group with 10 to 20 carbon atoms or an alkylaromatic group with 7 to 18 carbon atoms in the straight-chain or branched, saturated or unsaturated alkyl group and a linear or branched, unsaturated aliphatic group with 10 to 20 carbon atoms, m is 0 to 10, n is 1 to 15, M is an alkali metal, alkaline earth metal, ammonium or alkyl ammonium ion, with the degree of carboxymethylation being between 20 and 100% by weight.

4. The surfactant composition of claim 1, wherein the alkyl oligoglycoside has Formula (II), $$R'-O-Z_n \qquad (II)$$

wherein R' is a saturated or unsaturated, branched or unbranched alkyl group with 8 to 16 carbon atoms, $Z_n$ is an oligoglycosyl group containing an average of 1 to 1.45 hexose or pentose units or mixtures thereof.

5. The surfactant composition of claim 4, wherein the alkyl oligoglycoside has formula (II), wherein R' is a saturated or unsaturated, branched or unbranched alkyl group with 9 to 14 carbon atoms.

6. The surfactant composition of claim 4, wherein the alkyl glycoside has formula (II), wherein $Z_n$ is an oligoglycosyl group containing 1.1 to 1.45 hexose or pentose units or mixtures thereof.

7. The surfactant composition of claim 1, wherein the electrolyte thickener is selected from the group consisting of sodium chloride, ammonium chloride, sodium sulfate and magnesium sulfate.

8. The surfactant composition of claim 1, wherein said additive is a foam-strengthening, anionic surfactant.

9. The surfactant composition of claim 1, wherein the ratio of oxyethylate:oligoglyoside is between 5:1 and 1:10.

10. The surfactant composition of claim 9, wherein said ratio is between 2:1 and 1.5.

* * * * *